(12) United States Patent
Lederman et al.

(10) Patent No.: US 8,371,418 B2
(45) Date of Patent: *Feb. 12, 2013

(54) HEARING ASSISTANCE DEVICE

(76) Inventors: Jo Ann Lederman, Coral Gables, FL (US); Agustin Arrieta, Coral Gables, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/353,817

(22) Filed: Jan. 19, 2012

(65) Prior Publication Data

US 2012/0186899 A1    Jul. 26, 2012

Related U.S. Application Data

(63) Continuation-in-part of application No. 13/214,911, filed on Aug. 22, 2011, now Pat. No. 8,230,965, which is a continuation-in-part of application No. 13/011,506, filed on Jan. 21, 2011.

(51) Int. Cl.
H04R 25/00 (2006.01)
(52) U.S. Cl. ........................................... 181/129
(58) Field of Classification Search .................... 181/129
See application file for complete search history.

(56) References Cited

U.S. PATENT DOCUMENTS

| | | |
|---|---|---|
| 850,978 A | 4/1907 | Soares |
| 1,043,924 A | 11/1912 | Gottlieb |
| 1,292,083 A | 1/1919 | Sawyer |
| 1,820,107 A | 8/1931 | Agee |
| 1,950,839 A | 3/1934 | Chirila |
| 2,001,862 A | 5/1935 | Battey |
| 2,398,073 A | 4/1946 | Bonde |
| 2,443,481 A | 6/1948 | Sene |
| 2,509,157 A | 5/1950 | Lind |
| 2,537,201 A | 1/1951 | Amfitheatrof |
| 2,566,148 A | 8/1951 | Sky |
| 2,586,219 A | 2/1952 | Geffas |
| 2,625,931 A | 1/1953 | Phillips |
| 3,046,989 A | 7/1962 | Hill |
| 3,141,459 A | 7/1964 | Orcutt |
| 3,426,751 A | 2/1969 | Radewan |
| 3,531,090 A | 9/1970 | Laible |
| 3,742,943 A | 7/1973 | Malmin |
| 3,835,848 A | 9/1974 | Berner |
| 3,935,859 A | 2/1976 | Doyle |
| 3,976,066 A | 8/1976 | McCartney |
| 4,000,737 A | 1/1977 | Horn |
| 4,153,051 A | 5/1979 | Shippert |

(Continued)

FOREIGN PATENT DOCUMENTS

WO    WO 2012/100121 A2    7/2012

OTHER PUBLICATIONS

Everest, Alton. Master Handbook of Acoustics. Fourth Edition. 2001. [retrieved on Jul. 18, 2012]. Retrieved fron the internet: <http://wiki.dxarts.washington.edu/sandbox/groups/general/wiki/9e11b/attachments/012ef/The%20ear%20and%20the%20perception%20of%20sound%20-%20Alton%20Everest%20%28from%20The%20Master%20Handbook%20Of%20Acoustics%29.pdf?sessionID=c8b741b338c86cf7541bd02f23e6d9310610b6da>. Chapter 3, pp. 43-44.

*Primary Examiner* — Forrest M Phillips
(74) *Attorney, Agent, or Firm* — Malloy & Malloy, P.L.

(57) ABSTRACT

A device structured to assist the hearing of a user by being removably connected to and disposing a user's ear in an enhanced hearing orientation. One embodiment includes an elongated base, structured to be disposed in an operative position behind the user's ear. Opposite ends of the base include an adhesive material secured thereto, wherein different ones of said opposite ends are respectively disposed and maintained in confronting engagement with a rear surface of the ear and adjacently disposed portion of the user's head. The base further includes biasing capabilities disposed and structured to exert a sufficient, forwardly and outwardly directed positioning force on the user's ear to dispose and maintain it in the enhanced hearing orientation, when the base is in the operative position.

21 Claims, 10 Drawing Sheets

U.S. PATENT DOCUMENTS

| | | |
|---|---|---|
| 4,159,021 A | 6/1979 | Casburn |
| 4,187,838 A | 2/1980 | Dubrowski |
| 4,213,452 A | 7/1980 | Shippert |
| 4,274,402 A | 6/1981 | Shippert |
| 4,275,715 A | 6/1981 | Wolfe |
| 4,340,040 A | 7/1982 | Straith |
| 4,402,314 A | 9/1983 | Goode |
| 4,414,977 A | 11/1983 | Rezakhany |
| 4,534,342 A | 8/1985 | Paxa |
| 4,674,133 A | 6/1987 | Oschner |
| 4,768,613 A | 9/1988 | Brown |
| 4,771,859 A | 9/1988 | Breland |
| 4,823,789 A | 4/1989 | Beisang, III |
| 4,890,688 A | 1/1990 | Baker |
| 4,905,681 A | 3/1990 | Glascock |
| 4,932,943 A | 6/1990 | Nowak |
| 4,971,282 A | 11/1990 | Dickinson |
| 4,974,430 A | 12/1990 | Turner |
| 4,984,302 A | 1/1991 | Lincoln |
| 4,995,114 A | 2/1991 | Price, Jr. |
| 5,003,971 A | 4/1991 | Buckley |
| 5,020,629 A | 6/1991 | Edmundson et al. |
| 5,022,389 A | 6/1991 | Brennan |
| 5,101,837 A | 4/1992 | Perrin |
| 5,476,091 A | 12/1995 | Johnson |
| 5,533,499 A | 7/1996 | Johnson |
| 5,533,503 A | 7/1996 | Doubek et al. |
| 5,549,103 A | 8/1996 | Johnson |
| 5,920,636 A | 7/1999 | Oliveira et al. |
| 5,965,850 A | 10/1999 | Fraser |
| 6,039,751 A | 3/2000 | Hardee |
| 6,318,362 B1 | 11/2001 | Johnson |
| 6,817,440 B1 | 11/2004 | Kim |
| 7,028,343 B1 | 4/2006 | Watson |
| 7,093,600 B2 | 8/2006 | Sorribes |
| 8,122,995 B1 | 2/2012 | Riley |
| 8,230,965 B1 * | 7/2012 | Lederman et al. ............ 181/129 |
| 2002/0062110 A1 | 5/2002 | Sorribes |
| 2004/0188173 A1 | 9/2004 | Stilp |
| 2006/0151236 A1 | 7/2006 | McCool |
| 2007/0074991 A1 | 4/2007 | Heisserer |
| 2010/0059078 A1 | 3/2010 | Winters |

* cited by examiner

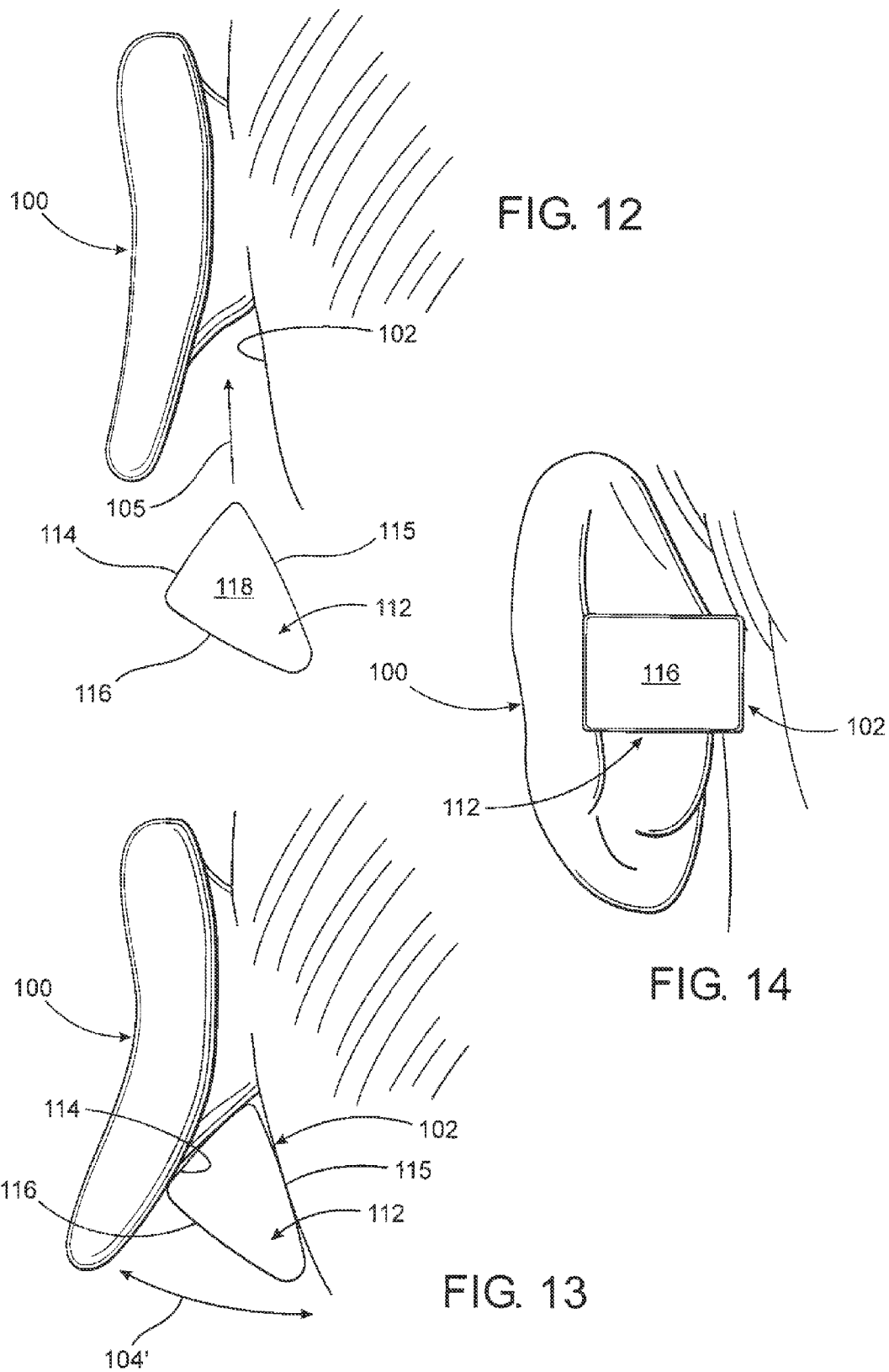

HEARING ASSISTANCE DEVICE

CLAIM OF PRIORITY

The present application is a continuation-in-part application of previously filed, now pending application having Ser. No. 13/214,911 filed on Aug. 22, 2011 now U.S. Pat. No. 8,230,965, which is a continuation-in-part application of previously filed, now pending application having Ser. No. 13/011,506, filed on Jan. 21, 2011, both incorporated herein by reference.

BACKGROUND OF THE INVENTION

1. Field of the Invention

This invention is directed to a hearing assistance device disposed and structured to be removably secured in an operative position behind the ear of the user. The device may or may not be disposed after use and in one embodiment includes biasing capabilities structured to exert a sufficient, forwardly and outwardly directed force on the ear to dispose and maintain it in an enhanced hearing orientation, when the hearing assistance device is in the operative position. Another embodiment relies primarily on a predetermined dimension and configuration, rather than a biasing force, to dispose the ear in the enhanced hearing orientation.

2. Description of the Related Art

Modern day hearing aids are typically electro-acoustic devices which fit in or behind a wearer's ear. As such, devices of this type are designed to amplify and modulate sound for the wearer. Moreover, every modern day electronic hearing aid comprises operative components including a microphone, loud speaker or receiver, battery and electronic circuitry. The electronic circuitry varies among devices and generally falls into different categories based on the type of audio processing (either analog or digital) and the type of control circuitry such as being adjustable or programmable.

Accordingly, modern technology has developed the electronic hearing aid to the point where the hearing impaired are no longer significantly disadvantaged in terms of interpreting speech and ambient sound. However, in earlier times such modern, electronic devices were, of course, not available. Instead, the individual who had difficulty hearing frequently relied on mechanical devices, such as, an "ear trumpet" or "ear horn". These devices were passive, funnel-like amplification cones designed to gather sound energy and direct it into or towards the ear canal. Modern day devices working on the same principal may generally include bone anchored hearing aids and/or cochlear implants. However, as previously used the "horn type" hearing aids included a tapered sound guide having an enlarged open end used to receive and optimize the transfer of sound from the air to the individual.

Additional developments in hearing aid technology has also led to relatively inexpensive disposable hearing aids powered by non-replaceable batteries. This type of hearing aid structure is designed to use power sparingly so that the included non-replaceable battery lasts for a reasonable length of time but for a much shorter duration than traditional hearing aids. Accordingly, disposable hearing aids are meant to overcome the task of battery replacement and other maintenance requirements such as adjustment, cleaning, programming, etc. Today a limited number of such disposable hearing aids are commercially available and are usable in different ways by the consumer.

Patients who benefit most from hearing aids are those who demonstrate a moderate to moderately severe hearing loss. These patients must wear hearing aids almost on a continuous basis. In contrast, persons who have a mild hearing loss may need amplification thereby not requiring the need, expense and possible discomfort in using a full time digital or analog hearing aid. Current recommendations for individuals with mild to moderate hearing loss and who are not hearing aid candidates include an attempt to decrease background or ambient noise, such as lowering the sound on televisions, turn off running water, etc. Also attempted conversation should be and/or is normally attempted to be conducted on a face to face basis.

Based on the above, there is a general belief that there is no available hearing enhanced device specifically for patients with mild to moderate hearing loss.

In determining the amount of assistance required from those individuals that are not necessarily candidates for a full-time hearing aid, it is important to note that the perception of loudness is not the same of the sound pressure level (SPL) associated with a given ear. Actually, the formulation for computing sound pressure level is relatively complex. However, an increase of ten decibels of the SPL is perceived to be approximately twice as loud as one would normally hear without any type of aid or beneficial assistance. A twenty decibel gain would seem to be approximately four times as loud. Therefore, perceptions of increases in decibel level of the SPL is generally as follows: an increase of one decibel represents an imperceptible change; an increase in three decibels is barely perceptible; an increase in five decibels is clearly noticeable; an increase in ten decibels is generally twice as loud and an increase of twenty decibels is generally about four times as loud.

Accordingly, there is a need in this industry for a hearing assistance device which is inexpensive, functional to at least minimally increase the ability to hear and which can be easily applied, removed, replaced, etc. when so desired. Such an improved, hearing device could be made available in standard or varied sizes, so as to be available to individuals of different ages/sizes, and also be structured to be applied in an operative position behind the ear of a wearer. Moreover, a preferred and proposed hearing aid of the type described could be extremely light weight and have an overall dimension and configuration which would allow a wearer or a user to substantially ignore its existence when conducting normal, everyday activities.

SUMMARY OF THE INVENTION

The present invention is directed to a device structured to mechanically assist the hearing ability of a user by the forced positioning and maintenance of the user's ear into an "enhanced hearing orientation", when the device is disposed in an operative position behind the user's ear. More specifically, the various preferred embodiments of the hearing assistance device include a base having a substantially elongated configuration of sufficient length to be disposed in the operative position relative to the user's ear. The base further includes opposite ends and an adhering structure or material such as, but not limited to, an adhesive composition disposed on a common side or common surface which is at least adjacent to the opposite ends. Alternately, the adhering structure can extend substantially along the entire length or at least a majority of the length of one side. Moreover, when used the adhesive material composition is hypoallergenic and as such, does not cause irritation or damage to the skin of the user to which the base is attached, even when disposed in the operative position for a relatively prolonged period of time.

Disposition of the base in the aforementioned operative position is dependent, at least in part, on the dimension, configuration and overall structure of the base. As such, the operative position comprises different ones of the opposite ends of the base being concurrently disposed into removable, confronting engagement with a rear surface of the ear and an adjacent portion of the head of the user. In the preferred operative position, the head portion of the user to which one of the opposite ends is removably attached is in overlying relation to a bone or hard tissue portion located behind and adjacent to the ear. Moreover, this adjacent, hard tissue portion of the head may include the temporal/mastoid portion of the user's skull.

As will be apparent, the base will be attached to the outer skin surface of the adjacent portion of the head as well as the outer surface of the skin of a rear portion of the ear. However, the disposition of one of the opposite ends in overlying at least partially supported relation to the "relatively unyielding" hard tissue portion of the user's head, facilitates the exertion of a sufficient, outwardly directed force on the ear, due to the biasing capabilities of the base, as set forth in greater detail hereinafter.

Accordingly, the various preferred embodiments of the hearing assistance device of the present invention include a base structured to have biasing capabilities. Moreover, the biasing capabilities of the base are disposed and structured to exert a pushing or positioning force or more specifically, a sufficient, forwardly and outwardly directed force on the ear to facilitate its disposition and maintenance in the aforementioned enhanced hearing orientation.

As a result, when the base of the hearing assistance device of the present invention is in the aforementioned operative position, the ear associated with the device will be "pushed" or forced outwardly from the adjacent head portion and forwardly towards the face or other frontal portion of the head into an orientation which significantly enhances the individual's ability to hear. The "enhanced hearing orientation" of the user's ear when influenced by the subject hearing assistance device is analogous to an individual placing his or her hand behind the ear in a substantially "cupped" configuration. This commonly applied cupping action by an individual with hearing difficulties disposes the ear in a more receptive orientation to receive directed and ambient sounds, thereby enhancing the individual's ability to hear.

Other structural and operative features of the various preferred embodiments of the present invention include at least one of the two opposite ends of the base having an enlarged configuration and dimension at least partially defined by an increased width or transverse dimension thereof. Alternatively, each of the opposite ends may have substantially equivalent dimensions and configurations, which cooperate with the biasing capabilities of the base to exert a sufficient force on the ear to force it outwardly and forwardly into the enhanced hearing orientation. For purposes of comfort, as well as practicality, the base further includes an intermediate portion which may be substantially equal in dimension to at least one of the opposite ends. However, in at least some of the embodiments of the hearing assist device, the intermediate device may have a lesser transverse dimension than the one opposite end disposed in confronting engagement with the rear surface of the ear, when the base is in the operative position.

In addition to the possible differences in dimension of the opposite ends and intermediate portions of the base, the one opposite end disposed in confronting engagement with the rear surface of the ear may also have an enlarged configuration such as a semi-circular peripheral configuration. Engagement of this opposite end with a sufficient rear surface portion of the ear is facilitated thereby assuring the exertion of a sufficient, forwardly and outwardly directed force thereon.

The adequacy of the positioning force is also determined by the inherent strength of the biasing capabilities associated with the base. Therefore, one preferred embodiment of the present invention includes the biasing capabilities being defined by at least one substantially elongated biasing member having "an inherent bias" extending along at least a majority or substantially the entire length of the base. In contrast, additional preferred embodiments of the present invention may be defined by the base being formed, in its entirety or in part, from a material having an inherent bias. In either case the biasing forces developed by the base should be sufficient to generate an adequate positioning force to dispose and maintain the ear in the enhanced hearing orientation, as set forth above.

For purposes of clarity, the term "inherent bias" as referred to herein is meant to include any material which when deformed from the orientation which it naturally assumes when not deformed, results in the development of a biasing force in the material, tending to orient it out of the deformed orientation into its naturally assumed orientation.

Accordingly, the various preferred embodiments of the hearing assistance device of the present invention overcomes many of the disadvantages and problems associated with electronic hearing aids or other mechanical type aids in terms of cost, effectiveness, comfort, convenience. Further, the device of the present invention facilitates the hearing of a user while being relatively unobtrusive. In addition, the hearing assistance device of the present invention may be disposable thereby further facilitating the ability of the user to easily apply, remove, and/or replace the device as desired.

Yet another preferred embodiment of the hearing assistance device comprises a base having a substantially solid, block-like configuration including a mostly or entirely solid interior structure. Moreover, the base includes a plurality of external sides wherein at least adjacent ones of the sides are disposed in transverse relation to one another. As set forth in greater detail hereinafter, the structurally preferred base of this embodiment may include at least three of such external sides. Also, when operatively disposed at least two of such external sides are disposed concurrently and independently in engaging relation to a rear surface of the ear and a substantially adjacent portion or surface of the head of the user behind the ear of the user.

Moreover, the substantially solid block structure or configuration of the base differs from the additional preferred embodiments of the hearing assistance device of this invention by being substantially or mostly absent any type of inherent or structurally enhanced biasing characteristics. In contrast, the base of this embodiment comprises a dimension and configuration which forces the ear to be disposed forwardly and outwardly from the head and thereby assume the enhanced hearing orientation, while the base maintains a substantially constant configuration and dimension.

As compared to the inherent biasing capabilities and/or characteristics of the other embodiments more specifically described in the elongated "strip-like" configuration thereof is typically structured to assume a normally planar or at least somewhat linear configuration, when not in its operative position. However, when the strip-like base is disposed in the operative position it is at least partially and initially bent or curved as it assumes its operative position behind the ear of the user. Thereafter, the inherent bias or structurally enhanced bias of the strip-like base tends to dispose the base in its original planar or linear configuration. As a result, these biasing capabilities exert a sufficient force on the ear to cause it to move forwardly and outwardly from the head and thereby assume the enhanced hearing orientation, as the strip-like base attempts to assume its planar or linear orientation.

In that the base of this additional preferred embodiment of the hearing assistance device includes a solid block structure or configuration, it typically will include no such biasing capabilities or characteristics or only a minimal degree thereof. In contrast to the strip-like base discussed above, the overall configuration of the solid block base will remain substantially constant, whether or not the base is in its operative position behind the ear of the user. As a result, when the solid block structure or configuration of the base is disposed in its operative position, its overall size and shape will result in the positioning of the ear forwardly and outwardly from the head into the aforementioned enhanced hearing orientation.

It is emphasized that the dimension and/over all configuration of the solid block base may in fact be at least minimally changed or altered while still being accurately defined as being "constant". By way of example only, the base may be formed of a minimally flexible or minimally resilient material such as some type of synthetic rubber, plastic, etc. which demonstrates the aforementioned minimal flexible and/or resilient characteristics. Therefore, when the solid block base is disposed in its operative position behind the ear of the user, it may be minimally reduced in size or minimally altered in configuration due to the forcing of the ear into the enhanced hearing orientation, as set forth above. As a result, the overall dimension and configuration of the solid block base remains and may be accurately described herein as being "substantially constant" while being at least minimally altered due to a particular material from which the base is formed.

Additional structural and operative features associated with the solid block base includes its dimensioning to define an interior thickness thereof being sufficient to exert the predetermined force on the ear to force or dispose it into the hearing enhanced orientation, when the base is in the operative position. This is also clearly distinguishable from the strip-like base embodiment of FIGS. 1-9, which is represented as including a minimal interior thickness between opposing surfaces of the elongated strip-like configuration.

Yet another preferred embodiment of the present invention is also directed to a device structured to facilitate hearing in a user's ear. As such, the hearing assistance device includes a base having an elongated configuration of sufficient length to assume an operative position relative to the ear, as well as a corresponding portion of the user's head. The base includes a head segment and an ear segment each including an appropriate adhering or connector structure disposed thereon. As with previously described preferred embodiments, the adhering structure may be in the form of an adhesive coating, film, etc. secured to a surface of the base which is disposed in confronting engagement to the rear skin surface of the ear and the outer skin surface of a corresponding and/or adjacent portion of the head of the user.

Accordingly, the aforementioned operative position comprises the head segment and the ear segment respectively and concurrently disposed in confronting engagement with the rear surface of the ear and the outer surface of the adjacent portion of the head. The base also includes biasing capabilities structured to produce a predetermined "pushing or positioning" force on the ear, by the confronting ear segment, when the base is in the operative position. Moreover, the base of the head segment and the ear segment are cooperatively structured in combination with the aforementioned biasing capabilities to determine that the positioning force is sufficient to dispose the ear into a "hearing enhanced orientation". As described in greater detail hereinafter, the hearing enhanced orientation is such that there is a preferably predetermined decibel increase in the sound pressure level (SPL) of the ear.

In more specific terms, the biasing capabilities are cooperatively structured with the remainder of the base to define the hearing enhanced orientation as an outwardly and forwardly positioning of the ear relative to the adjacent and/or corresponding portion of the head, such as at least that portion of the head which is engaged by the head segment of the base. Therefore, the base and the biasing capabilities are cooperatively structured to define the hearing enhanced orientation as being dependent on the strength of the positioning force. As cooperatively utilized, the hearing enhanced orientation relative to the user's head is determinative of an increase or decrease in the decibels of the sound pressure level (SPL) of the corresponding ear. Therefore, the farther the ear of the user is disposed outwardly and forwardly from the user's head, the greater the increase in decibel of the sound pressure level, within certain acceptable and/or practical ranges. In cooperation therewith, a reduction or lessening of the forwardly and outwardly positioning of the user's ear, relative to the head, will result in a decrease in the decibels of the sound pressure levels.

By way of example and dependent on the hearing capabilities or limitations of the user, the base and the corresponding biasing capabilities may be such as to develop a pushing or positioning force which orients the ear sufficiently outwardly and/or forwardly from the head to establish an increase of at least 5 decibels in the sound pressure level. In the alternative, a pushing or positioning force may be developed which is sufficient to establish an increase of at least 10 decibels in the sound pressure level. Further by way of example, the biasing capabilities of a given base may be structured to create a pushing force sufficient to establish an increase of generally about 20 decibels in the sound pressure level. Therefore, as practically and preferably applied, the base, head segment and ear segment are structured in cooperation with the biasing capabilities to establish a pushing or positioning force which is sufficient to result in an increase of generally between 5 decibels and 20 decibels of the sound pressure level, as compared to the sound pressure level of the ear when it is disposed in a normal orientation, without any pushing or positioning force being exerted thereon. As should be apparent, the needs and/or hearing capacity of the individual utilizing the hearing assistance device will be determinative of an appropriate increase in decibels of the sound pressure level.

An additional structural and operative feature of the preferred embodiment of the present invention comprises the head segment having a larger transverse dimension along a majority of its length than that of the ear segment. Further by way of describing at least one practical application, the transverse dimension of the head segment may be generally about ¾ of an inch extending along the majority of its length. In addition, the length of the head segment may also generally be about ¾ of an inch as it extends between its junction or connection with the ear segment and an outer extremity of the ear segment. Further structural features include the ear segment comprising an elongated configuration of substantially continuous transverse dimension along its length, substantially from its connection or junction with the head segment to an outer extremity or the free end of the ear segment. Moreover, the transverse dimension of the head segment may be at least generally about ¼ of an inch, wherein a length of the head segment is at least generally about ¾ of an inch.

The biasing capabilities of this preferred embodiment comprises the structuring of the base to include at least one biasing member or rib having an elongated configuration.

Moreover, the elongated rib or biasing member is structured to include an inherent bias such that it will normally be biased into a substantially linear configuration when not disposed in the aforementioned operative orientation. In addition, this preferred embodiment of the reinforcing rib is that it is dimensioned and configured to extend along substantially the entire length of the base including substantially the entire length of both the ear and head segment. Accordingly and further by way of example, the biasing rib is generally about 1½ inches as it extends concurrently along the lengths of the head segment and ear segment, as set forth above.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 12 is a top view of the ear and correspondingly head portion of the user, wherein the additional preferred embodiment of FIGS. 10 and 11 is ready for placement in its operative position.

FIG. 13 is a top view of the embodiment of FIG. 12 wherein the additional preferred embodiment of the hearing assistance device is in its preferred, operative position.

FIG. 14 is a rear view of the embodiment of FIG. 13.

Like reference numerals refer to like parts throughout the several views of the drawings.

DETAILED DESCRIPTION OF THE PREFERRED EMBODIMENT

Figure 1:
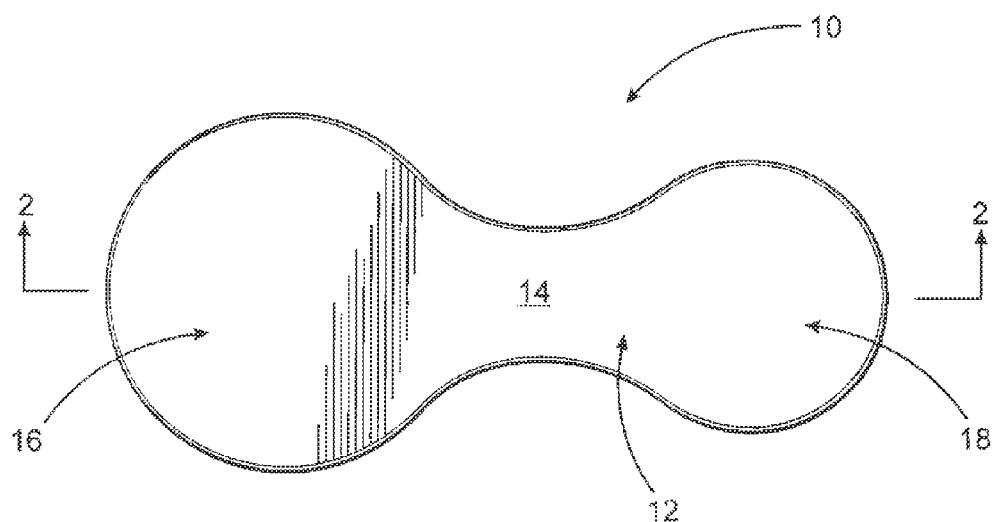
FIG. 1 is a front plan view of one preferred embodiment of the hearing assistance device of the present invention.

As represented in the accompanying drawings, the present invention is directed to hearing assistance device generally indicated as 10 including an elongated base 12. The base 12 comprises an intermediate portion 14 disposed in interconnecting relation between two oppositely disposed ends 16 and 18. In addition, an adhering structure or material, such as a hypoallergenic adhesive 20, is disposed on an underside of the base 12 which is common to both the oppositely disposed first and second opposite ends 16 and 18 respectively. In the embodiment represented in FIG. 2, the adhering material or adhesive 20 may also extend along substantially the entire length of the corresponding, under surface and thereby extend along at least a portion of the length of the intermediate portion 14.

The base 12 has a sufficient length to assume and be disposed in an operative position, as generally represented in FIGS. 3-6, behind ear 100 of a user or wearer of the hearing assistance device 10. Moreover, the provision of the adhering material or adhesive 20 will serve to removably but securely maintain the base 12 in the operative position for relatively prolonged periods of time. However, the adhering characteristics of the material 20 are such as to facilitate removal of the base 12 from the operative position easily and quickly without irritation or damage to the portions of the skin of the user engaged by the base 12.

Additional, structural and operative features of the hearing assistance device 10 and specifically including the base 12 comprise the provision of biasing capabilities in the base 12. More specifically, the biasing capabilities are such as to exert a "pushing or positioning" force or more specifically a sufficient, forwardly and outwardly directed force on the ear 100 to dispose it in an "enhanced hearing orientation". Moreover, the biasing force will be sufficient to maintain the ear 100 in the enhanced hearing position for a prolonged period of time, as long as the base 12 is in the operative position behind the ear, as represented in FIGS. 3-6 and explained in greater detail hereinafter.

More specifically, the aforementioned biasing capabilities are structured to be incorporated in the base and may take the form of the material 22 from which the base 12 is formed. Therefore, in the embodiment of FIGS. 1 and 2, the material 22 from which the base 12 is formed includes an "inherent bias" which serves to position and maintain the base 12 in a naturally assumed orientation. As such, the natural orientation of the base 12 may include, but is not limited to, a substantially in-line or at least partially planar orientation. However, when the base 12 is selectively disposed or forced into a curved, bent or other predetermined deformed orientation, a biasing force is developed therein which tends to bias the base into the aforementioned naturally assumed or substantially planar orientation. Such an inherently biased material may include various types of plastic, natural or synthetic rubbers or other flexible material compositions which are specifically structured to include the aforementioned inherent bias tending to dispose the base in its naturally assumed orientation such as, but not limited to, that represented in FIG. 2.

Figure 2:
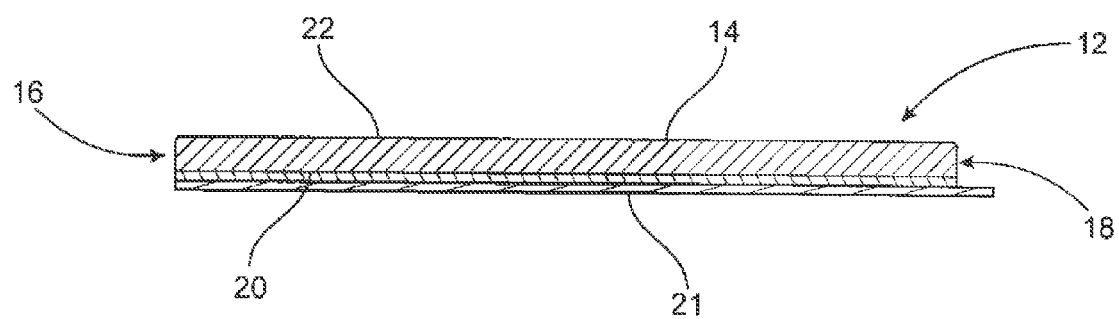
FIG. 2 is a side view along line 2-2 of FIG. 1.
Figure 9:
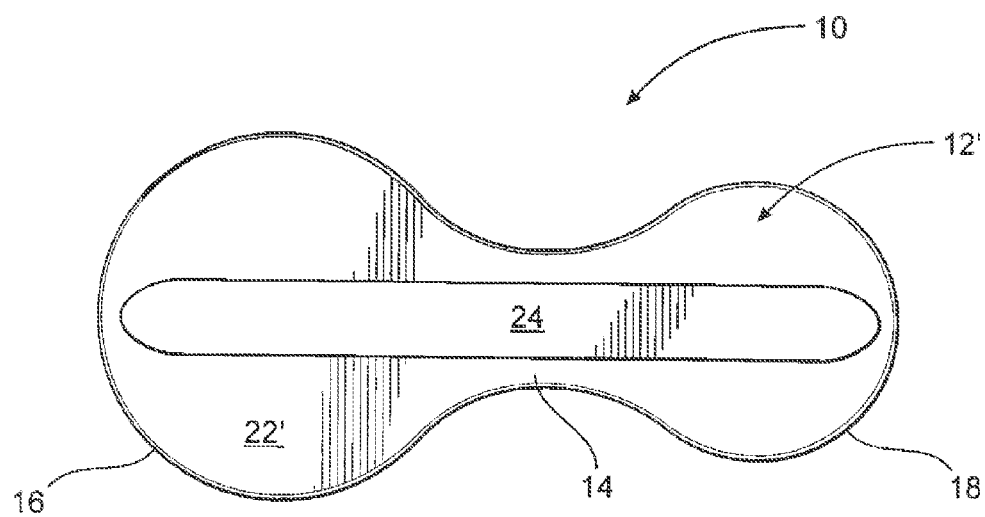
FIG. 9 is a front plan view of yet another preferred embodiment of the hearing assistance device of the present invention.
Figure 10:
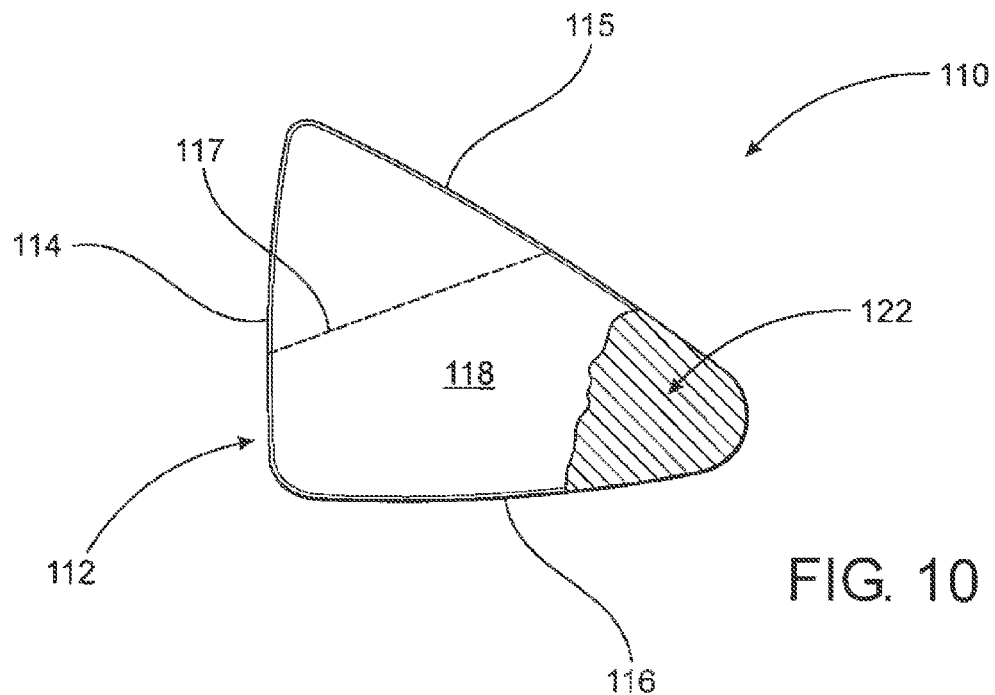
FIG. 10 is a top view of yet another embodiment of the hearing assistance device of the present invention.
Figure 11:
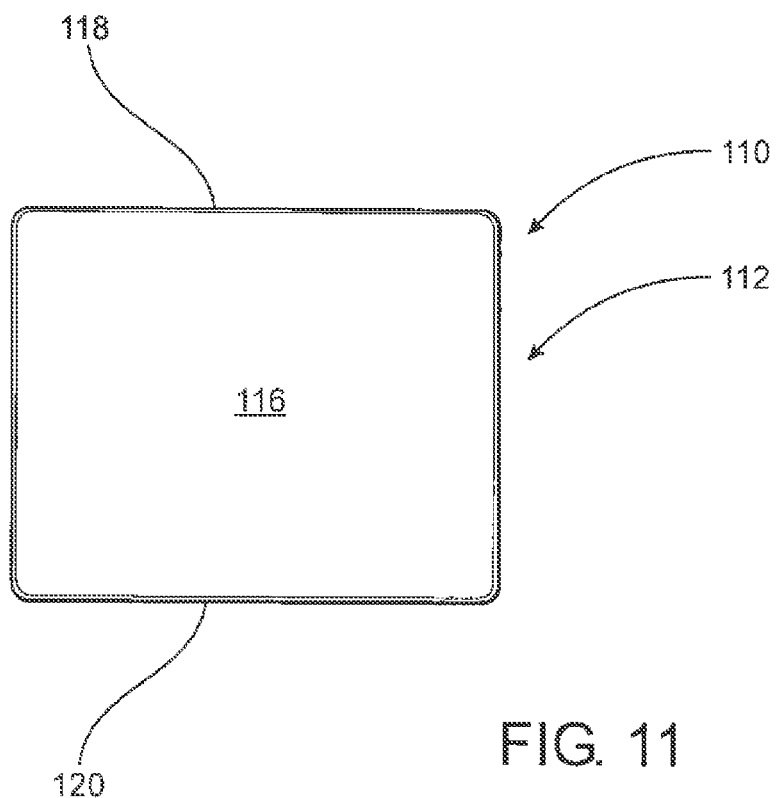
FIG. 11 is an end view of the embodiment of FIG. 10.
Figure 15:
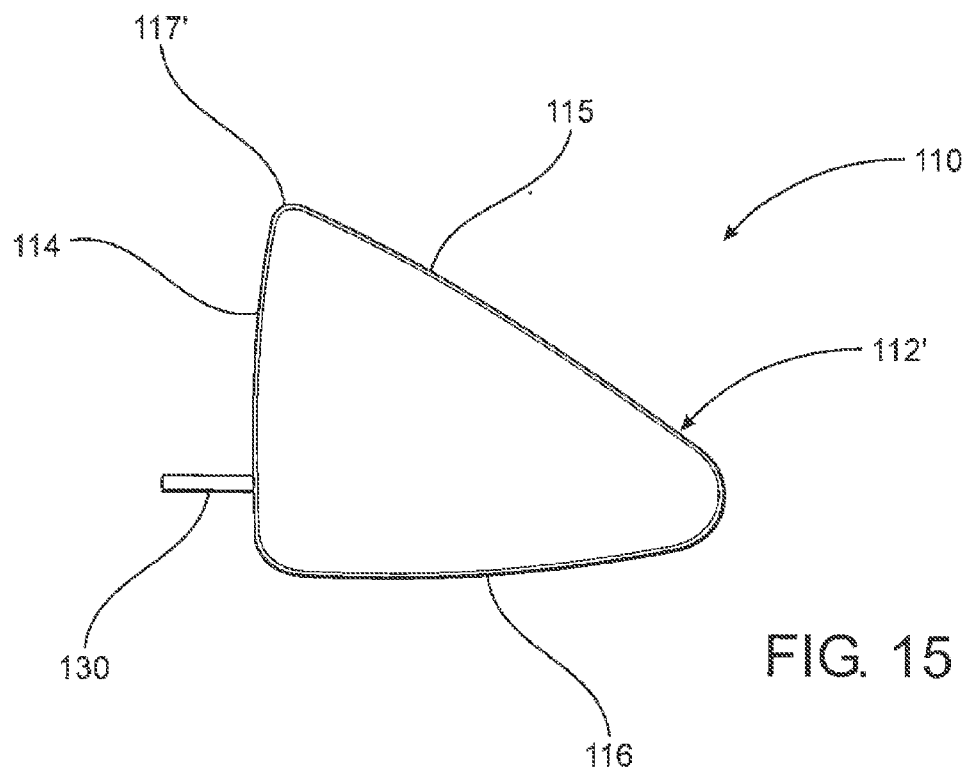
FIG. 15 is a top view of yet another preferred embodiment of the additional preferred embodiment of FIGS. 10 and 11.
Figure 16:
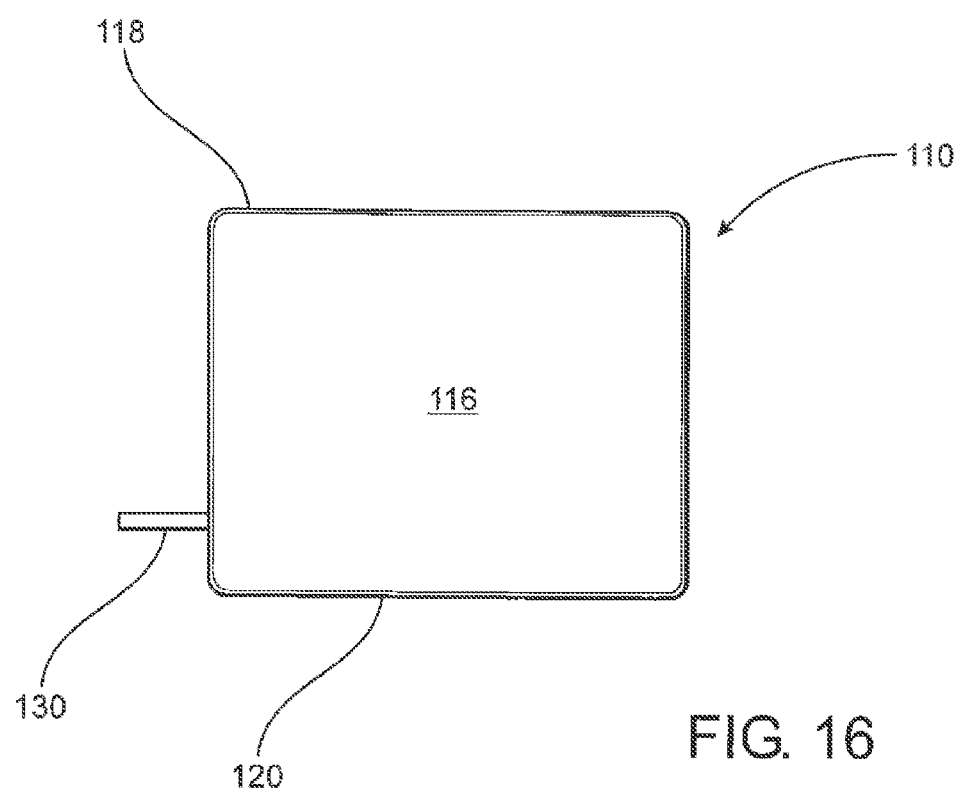
FIG. 16 is an end view of the embodiment of FIG. 15.

In contrast the embodiment of FIG. 9 discloses a base 12' formed of a material 22' which may not have the same degree of "inherent bias" as a material 22 from which the embodiments of FIGS. 1 and 2 are formed. As such, the biasing capabilities incorporated within the base 12' comprises a biasing member 24 secured to the base 12'. More specifically, the biasing member 24 has an elongated configuration and is mounted on or within the base 12' so as to extend along at least a majority of the length thereof. Alternatively the biasing member 24 may extend substantially along the entire length, as represented in FIG. 9. Moreover, the biasing member 24 has the aforementioned "inherent bias" which serves to normally dispose the member 24 into its original and possibly in-line or planar orientation. Structural modifications of the embodiment of FIG. 9 include the biasing member 24 being mounted on or secured to the base 12' by being integrally or fixedly secured to the exterior surface thereof so as to move therewith. Alternatively, the biasing member 24 may be disposed on the interior of the base 12' and be integrally formed therewith during the production or formation of the base 12'. It is emphasized, that while the structural features of the biasing capabilities of embodiments of FIGS. 1, 2 and 9 may vary, as set forth above, the operative features of each of these embodiments are such as to exert a sufficient, forwardly and outwardly directed force on the ear 100 of the user, as schematically represented as 104, when the base 12, 12' is disposed in the operative position of FIGS. 3-6.

As set forth above and as represented in FIGS. 3-6, the operative position of the base 12, 12' is schematically represented. Moreover, the preferred operative position is more specifically defined by one of the opposite ends, such as the first opposite end 16, being removably but securely disposed in confronting engagement with the rear surface of the ear 100 on the back side thereof. In addition, the operative position is further defined by the opposite end, such as the second opposite end 18 being removably but securely disposed in confronting engagement with the skin 102 which overlies the hard tissue portion of the user's head located adjacent the back side of the rear surface of the ear 100. This adjacent hard tissue portion of the head may be more specifically described as the bone which underlies the skin 102 and may be more accurately referred to as the temporal bone and/or the mastoid portion thereof.

Figure 3:
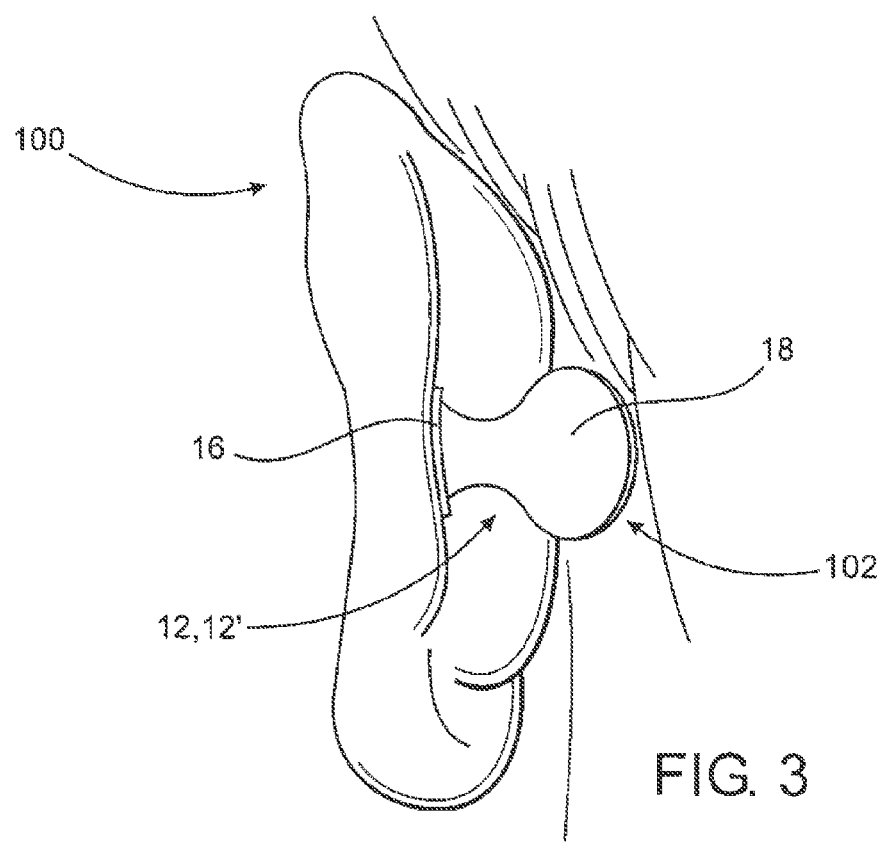
FIG. 3 is a rear view of the embodiment of FIGS. 1 and 2 disposed in an operative position behind the user's ear.
Figure 4:
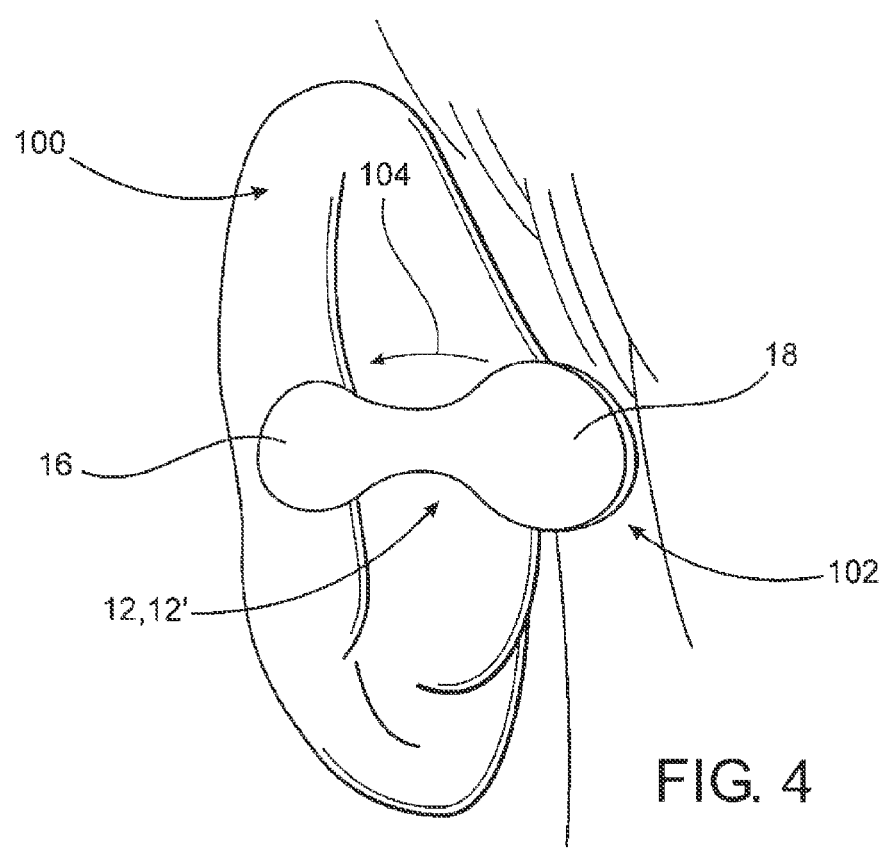
FIG. 4 is a rear view of the embodiment of FIG. 3 wherein the hearing assistance device is exerting a force on the ear sufficient to dispose the ear in an enhanced hearing orientation.
Figure 5:
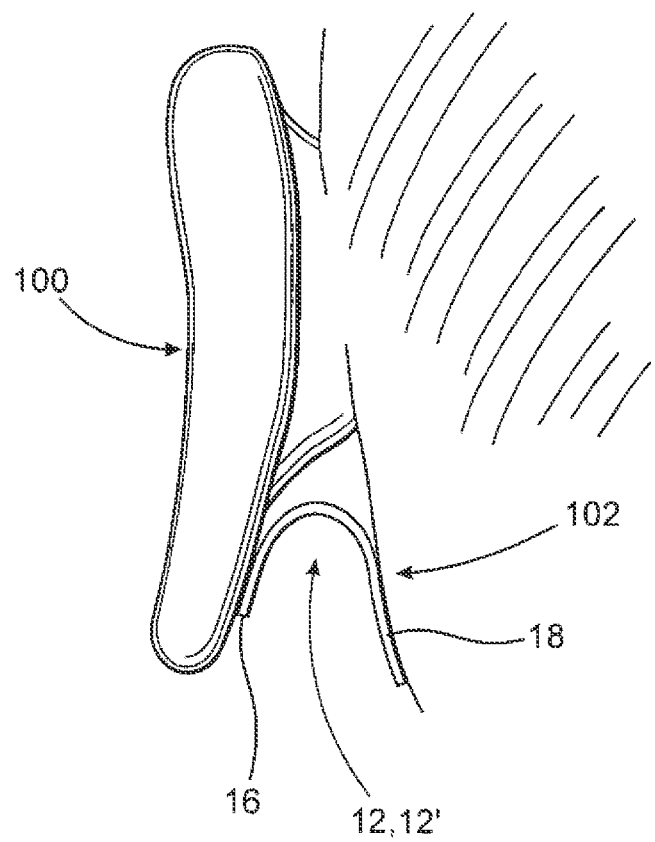
FIG. 5 is a top view of the embodiment of FIG. 3.
Figure 6:
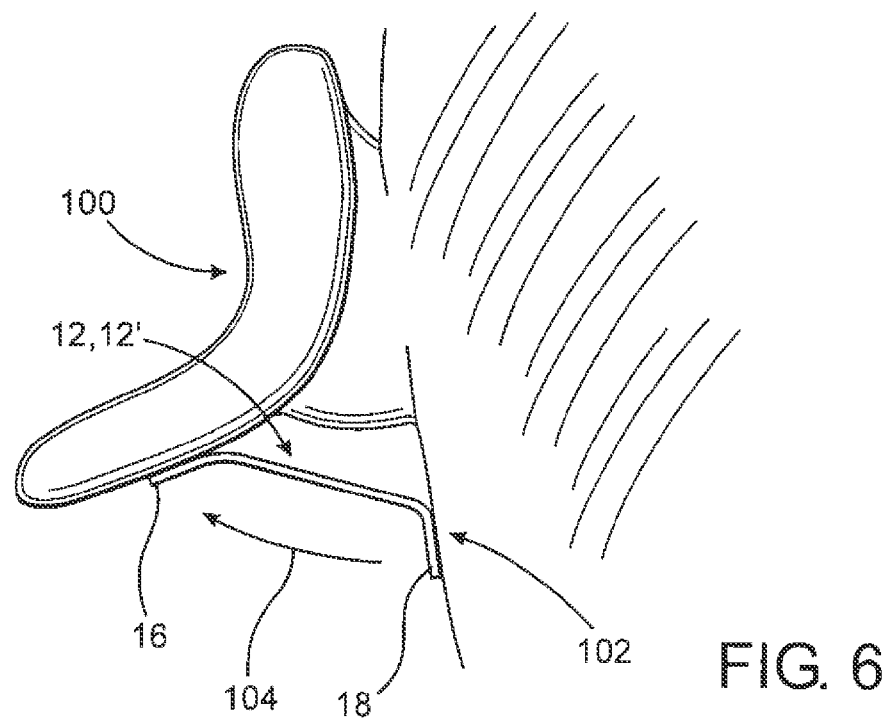
FIG. 6 is a top view of the embodiment of FIG. 4.

Therefore, when the base 12, 12' of the hearing assistance device 10 is initially disposed in the operative position, represented throughout the indicated FIGS. 3-6, it may naturally assume a bent, partially folded and/or substantially curved orientation such as represented in FIGS. 3 and 5. However, due to the aforementioned and described inherent bias associated with each of the bases 12 or 12', it will be disposed and structured to exert a sufficient "pushing or positioning" force or sufficient, forwardly and outwardly directed force 104 on the ear 100. As a result of the pushing force 104, the ear 100 will be disposed and maintained in the "enhanced hearing orientation", as represented in FIGS. 4 and 6, as long as the base 12, 12' is in the operative position behind the ear 100.

With further reference to FIGS. 4 and 6 and as set forth above, the ear 100 is represented in the enhanced hearing orientation. This enhanced hearing orientation is accomplished by the inherent bias incorporated within the base 12 or 12' forcing the first opposite end 16 disposed in confronting engagement with the rear or backside portion of the ear 100 outwardly due, at least in part, to the flexible nature of ear 100. In contrast, the opposite or second end 18 is removably secured to the aforementioned adjacent, hard tissue portion of the head. This hard tissue portion is not flexible or does not "yield" in reaction to the biasing force exerted thereon by the base 12 or 12'. Therefore, the biasing force exerted by the base 12 or 12', due to the aforementioned "inherent bias" incorporated therein, will result in the exertion of a sufficient, forwardly and outwardly directed force 104 on the ear 100. The force 104 will thereby be sufficient to dispose and maintain the ear 100 in the enhanced hearing orientation, as represented in FIGS. 4 and 6, when the base 12 or 12' is in the operative position, as described in detail above.

Moreover, the "enhanced hearing orientation" as schematically represented in FIGS. 4 and 6 will serve to enhance the hearing ability of the user of the device 10 by having a similar effect as that provided by the commonly recognized "cupping action" employed by numerous individuals which suffer from a hearing loss. Such a forwardly and outwardly directed orientation of the ear 100 disposes the interior or ear canal of the ear 100 in a better position to receive the sound waves existing in the ambient environment in which the user of the hearing assistance device 10 is located.

Figure 7:
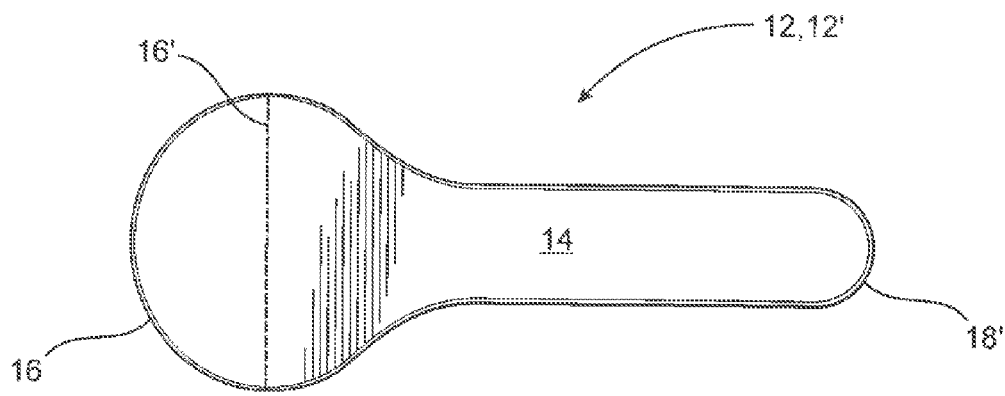
FIG. 7 is front plan view of yet another preferred embodiment of the hearing assistance device of the present invention.
Figure 8:
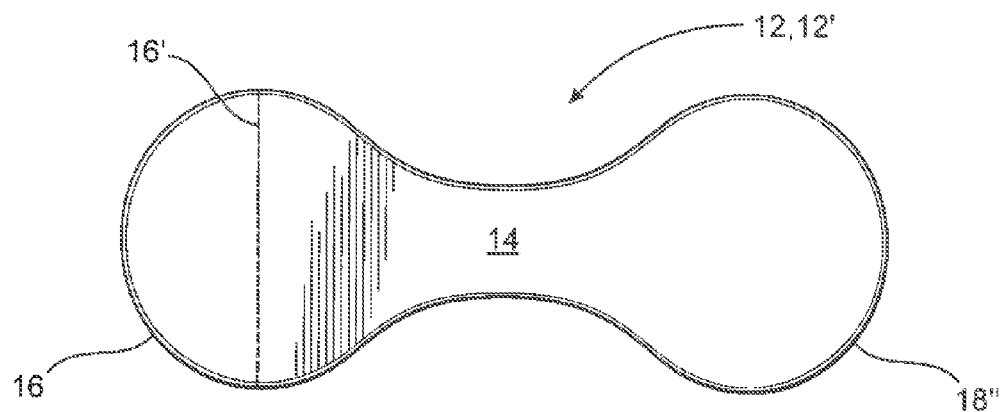
FIG. 8 is a front plan view of yet another preferred embodiment of the hearing assistance device of the present invention.

As set forth above, the hearing assistance device 10 includes the base 12 or 12' having an elongated configuration of sufficient length to selectively dispose and maintain the base 12, 12' in the operative position behind the ear 100 of the user. However, in order to further facilitate positioning of the ear in the enhanced hearing orientation of FIGS. 4 and 6, the configuration of the base 12 and 12' may vary. As represented in FIGS. 7 and 8, different structural configurations of either the base 12 or 12' are disclosed. More specifically, the first opposite end 16 in the embodiment of FIG. 7 has a larger overall dimension including a larger transverse dimension 16' than that of either the intermediate portion 14 or the second opposite end 18'. With regard to FIG. 8, the overall dimension of the first opposite end 16 including the transverse dimension 16' is greater than the intermediate portion 14 and substantially the same as that of the second opposite end 18'. Therefore, in the embodiments of FIGS. 1, 2, 7 and 8, the first opposite end 16 includes an overall dimension and a transverse dimension 16' which is at least as great as the second opposite end 18 and 18" and preferably greater than the second opposite end 18', as well as the intermediate portion 14. As a result, the aforementioned forwardly and outwardly directed force 104 exerted on the ear 100 may be further facilitated by removably securing the first opposite end 16 to the rear surface or backside portion of the ear 100 as clearly represented.

Yet another preferred embodiment of the hearing assistance device of the present invention is represented in FIGS. 10-16 and is generally indicated as 110. More specifically, the hearing assistance device 110 includes a base 112 having a substantially solid block structure or configuration which is distinguishable from the elongated "strip-like" configuration of the base 12, 12' of the embodiments represented in FIGS. 1-9. The base 112 may be formed from a variety of different materials including relatively hard, solid and possibly rigid plastic, synthetic rubber, etc. However, for purposes of comfort to the user, such as when the base is in its operative position, the base 112 may also be formed of a "softer" plastic, synthetic rubber, or other appropriate material. As such, the base 112 may demonstrate a minimal amount of flexibility or resiliency, such as when being handled and/or being disposed in the operative position as represented in FIGS. 12-14. It is emphasized that the material from which the base 112 is formed should have sufficient physical characteristics that allow the base 112 to maintain a "substantially constant" configuration and/or dimension whether or not it is in its operative position.

The solid, block configuration of the base 112 is more specifically defined by a plurality of external sides 114, 115, 116. The number of sides 114-116 may vary, however, in the preferred embodiment of FIGS. 10-16, the plurality of external sides are at least three in number. As also represented, the plurality of external sides 114-116 collectively define the external lateral periphery or overall exterior peripheral configuration of the base 12 as they collectively and continuously extend about the lateral or side portion thereof. The base 112 also includes top or upper surface or end 118 and a bottom or under surface or end 120. Therefore, while the base 112 is accurately referred to as having a solid, block configuration and while the plurality of external sides 114-116 may vary in number and size, the base 112, as represented in FIGS. 10-16 may include a generally "wedge-shape".

The solid, block configuration of the base 112 may be further be defined and accurately described as including a solid structure interior 122 formed of an appropriate material as set forth above. The solid structure material 122, while possibly demonstrating a minimal amount of flexibility or resiliency, provides sufficient structural integrity to the base 112 to maintain it in the "substantially constant" overall configuration and dimension when it is in the operative position of FIGS. 13 and 14 or when it is not in such an operative position as represented in FIGS. 10-12 and 15, 16.

Therefore, while the embodiment of the base 12 and/or 12' as demonstrated in FIGS. 1-9 has a generally elongated, linear and/or substantially planar configuration when not in its operative position, it is at least initially bent or curved as demonstrated in FIGS. 3 and 4 to assume its operative position. As a result, the base 12 and/or 12' includes an inherent or structurally added bias which tends to position the base 12 or 12' in the aforementioned linear or planar orientation. Due to such enhanced bias, the operative features of the base 12 and/or 12' facilitate the disposition of the ear 100 into the hearing enhanced orientation of FIGS. 4 and 6.

In contrast, the base 112 of the embodiments of FIGS. 10-16 does not primarily rely on any inherent biasing characteristics, as set forth above. Instead the base 112 will maintain a substantially constant configuration and/or dimension whether or not it is in the operative position of FIGS. 13 and 14 or not. Accordingly, the forcing of the ear 100 into the enhanced hearing orientation as demonstrated in FIG. 13 is based primarily on the overall size and/or configuration of the base 112 relative to the ear 100 and corresponding surface 102 of the head portion of the user. More specifically, the dimensional and configurational characteristics of the base 112 will force the ear 100 into the hearing enhanced orientation as represented in FIG. 13 when the base 112 is in the operative position.

With primary reference to FIGS. 12-14, the base 112 is represented as being ready for disposition in its operative position in accordance with directional arrow 105. When so disposed, the operative position of the base 112 is defined by two adjacent, transversely oriented surfaces, as at 114 and 115, being disposed in confronting engagement and/or removal connection with the rear surface of the ear 100 and the correspondingly disposed surface 102 of the head of the user, as also explained in detail above with regard to the embodiment of FIGS. 1-9. When so disposed, the substantially constant dimension and configuration of the base 112 will force the corresponding portion of the ear 100 in a forwardly and outwardly direction and into the aforementioned enhanced hearing orientation, as schematically represented by directional arrow 104'.

Additional structural features further defining the fixed or constant dimension and/or configuration of the base 112, whether or not it is in its operative position of FIGS. 13 and 14, is the solid structure 122 of the interior of the base 12 having an interior thickness 117, such as extending between two adjacent and transversely oriented surfaces 114 and 115, being substantially constant whether or not the base 112 is the operative position. For purposes of clarity only, such an internal thickness 117 between adjacent surfaces 114 and 115 is schematically represented in phantom lines and provided for purposes of clarity. Moreover, the interior thickness of said solid block or structure configuration is not only substantially constant, but is sufficiently dimensioned to force the ear forwardly or outwardly from the head and into the enhanced hearing orientation, when the base is in the operative position.

Additional structural features of the hearing assistance device 110 include the provision of a penetrating member 130 secured to the base 112' and extending outwardly from one of plurality of external sides, as at 114, which is disposed in confronting relation to the rear surface of the ear 100. The penetrating member 130 is disposed and structured to penetrate and pass through a correspondingly disposed part of the ear 100 such as, but not limited to, the earlobe. As such, the penetrating member 130 may at least partially define an earring post or like structure to which an earring or other decorative or utilitarian device may be attached when it is disposed on the exterior surface of the ear. In addition, when the penetrating member 130 is attached to and extends outwardly from one of the external sides, as at 114, the base 112' may be modified in its size, configuration and/or disposition so as to accommodate the of the penetrating member 130 in a location to substantially align with the portion of the ear 100 which is to be pierced.

Yet additional features include the provision of an adhering material disposed on and at least partially covering at least one but more practically a plurality of the plurality of external sides, such as at 114 and 115. This adhering material may be used to removably connect or attach the corresponding surfaces 114 and 115 to a rear surface of the ear 100 and a corresponding surface 102 of the head of the user. As with the embodiments of FIGS. 1-9, the adhering material may be a hypoallergenic adhesive 20 which will prevent or significantly resist irritation to the skin surface to which the external sides 114 and 115 are attached.

Figure 17:
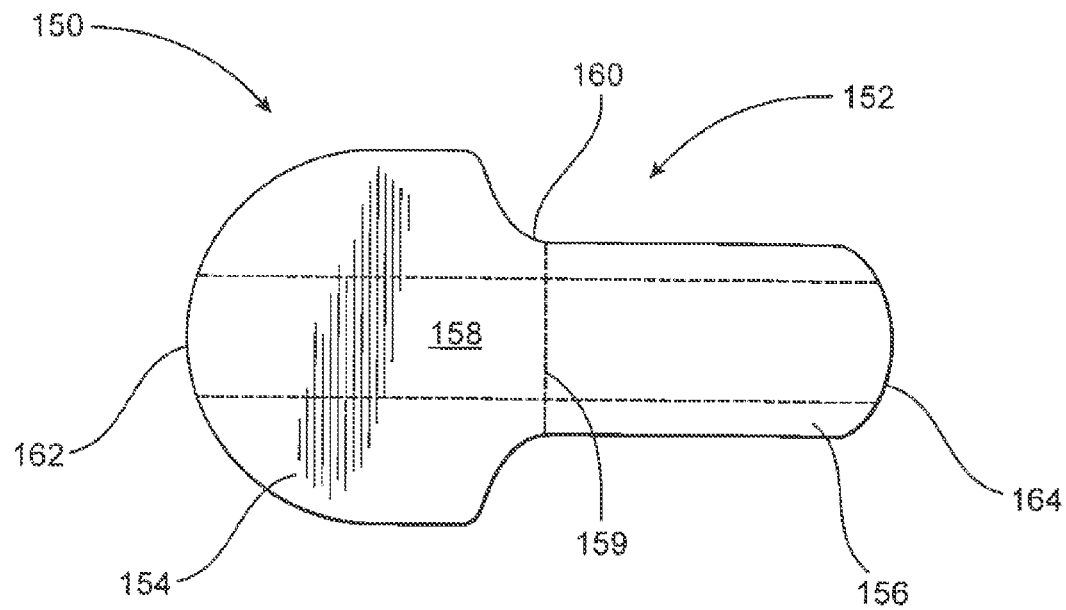
FIG. 17 is a front view of yet another preferred embodiment of the hearing assistance device.

FIG. 17 represents yet another preferred embodiment of the hearing assistance device, generally indicated as 150. As such, the device 150 includes a base 152 including a head segment 154 and an ear segment 156. As such, the hearing assistance device 150 is similar in operation and effect to the additional preferred embodiments and serves to facilitate enhanced hearing in a user's ear with which the device 150 is associated. However, the structural features are distinguishable from the embodiments of FIGS. 1 through 16, as will be described in greater detail hereinafter.

Figure 18:
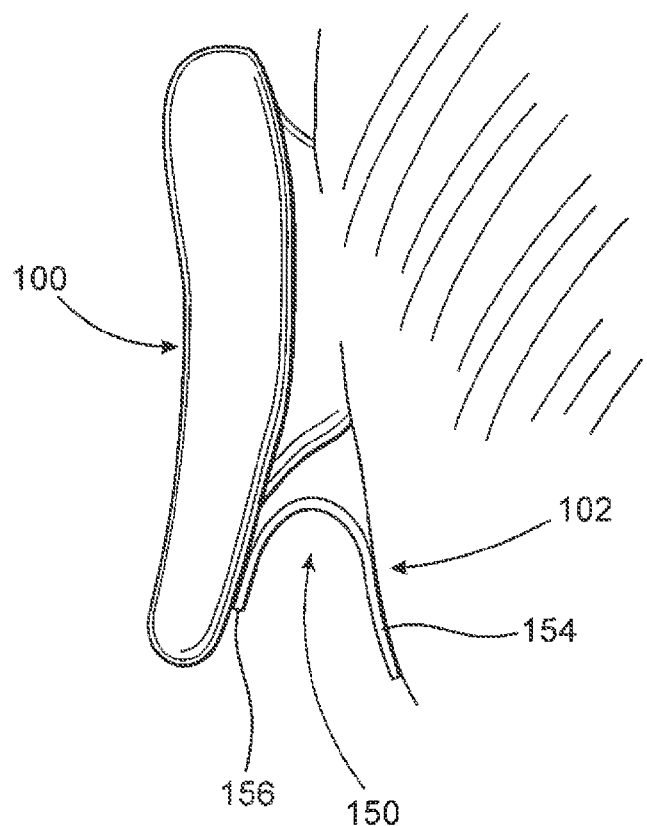
FIG. 18 is a top view of the embodiment of FIG. 17 in an operative position and exerting a pushing or positioning force on the ear sufficient to dispose it in an enhanced hearing orientation.
Figure 19:
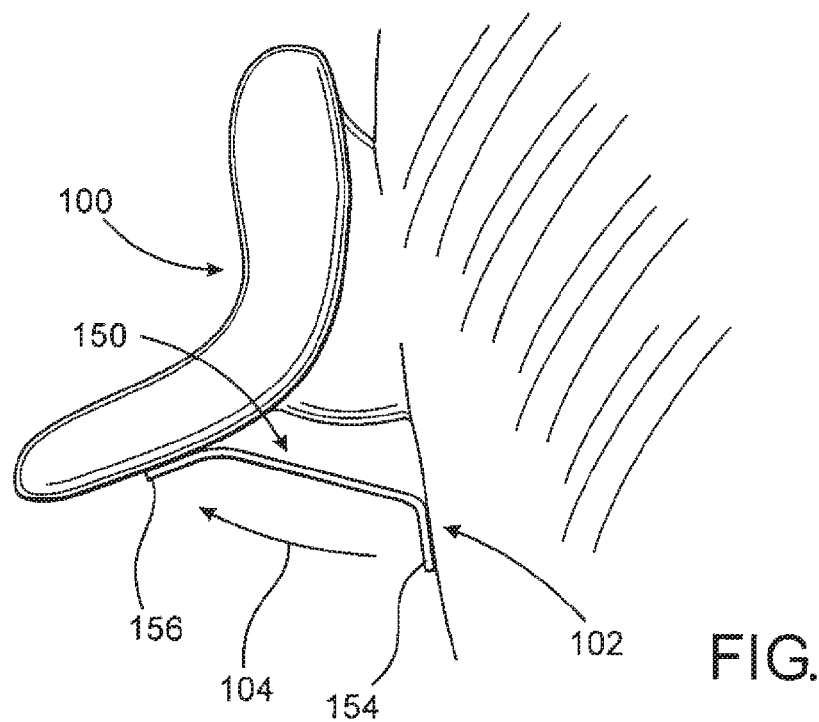
FIG. 19 is a top view of the embodiment of FIG. 17 wherein the hearing assistance device is exerting a pushing or positioning force on the ear, greater than that demonstrated in FIG. 16 and being sufficient to dispose it in a more pronounced enhanced hearing orientation.

The hearing assistance device 150 is dimensioned, configured and structured to be disposed in an operative position generally as represented in FIGS. 18 and 19. The configuring of the hearing assistance device 150 can be accomplished by a bending or curving thereof into the shape depicted in FIG. 18. Moreover, the hearing assistance devices 150 may include an indicator 159, which may be in the form of fold line, crease, indicia, marking or other means of determining where the base 152 of the hearing assistance device 150 is to be bent or curved. As further demonstrated in FIG. 18 the configuring of the hearing assistance device will be in a direction substantially away from the adhesive 20 and/or protective liner 21. Once the configuring is completed, the liner 21 is removed, exposing the adhesive composition 20 and facilitating the attachment of both the ear segment and head segment.

In accomplishing placement of the hearing assistance device in the operative position, the portion of the base 152 directly corresponding to the indicator 159 is disposed behind the ear 100 and in substantially aligned or possibly confronting relation with the "junction" of the ear 100 and the head. As such the ear segment 156 is disposed in confronting engagement with rear skin surface, behind a user's ear 100. Concurrently, the head segment 154 is disposed in confronting engagement with the skin surface of an adjacent or corresponding portion of the user's head, as at 102 in FIGS. 18 and 19. In addition, the surface or surfaces of the hearing assistance device 150 that is disposed in confronting engagement with the corresponding skin surfaces of the ear and head include a connector or adhering structure serving to facilitate the secure but removable attachment of the device 150 in the aforementioned operative position. Such a connector may be in the form of an adhesive or other appropriate type connector generally indicated as 20 in the embodiment of FIG. 2.

Additional structural features of the hearing assistance device 150 include biasing capabilities preferably in the form of a biasing member or rib 158, extending along substantially the entire or at least a majority of the length of the base 150. As represented, the biasing member 158 concurrently extends along the length of both the head segment 154 and the ear segment 156. Moreover, the biasing member or rib 158 may be at least partially disposed on the interior of the base and/or appropriately positioned and/or integrally or fixedly mounted on exterior portions thereof. In either structural modification, the biasing rib 158 is structured to include an inherent bias which normally tends to position or "bias" the rib 158 and well as the base 152 into a substantially linear or planar orientation. As used herein, the term planar is not necessarily intended to describe a true flat, plane. To the contrary, the inherent bias of the reinforcement of the rib 158 tends to normally dispose the base 152 in an outwardly elongated configuration as represented in FIG. 17. Accordingly, the reinforcement member or reinforcement rib 158 defines "biasing capabilities" of the base 152 which is operative to produce a predetermined pushing or positioning force on the ear 100, by the head segment 154, when the base 152 is in the operative position of FIG. 18 or 19.

Accordingly, when the base 152 is in the operative orientation of FIG. 18 or 19 the biasing capabilities at least partially defined by the reinforcement rib 158, along with the cooperative structuring and disposition of the head segment 154 and ear segment 156 exerts a predetermined "pushing or positioning" force on the ear so as to substantially position it into any one of a possible plurality of hearing enhanced orientations. More specifically, as is clearly demonstrated in FIGS. 18 and 19, the hearing enhanced orientation of the ear may be at least partially defined by an outwardly and forwardly positioning of the ear 100 relative to the corresponding head portion 102.

It is emphasized that the "strength" of the pushing or positioning force is determinative of the hearing enhanced orientation of the ear 100. Further the hearing enhanced orientation of the ear 100 relative to the corresponding portion of the user's head 102 is determinative of an increase or decrease of the decibels of the sound pressure level of the ear 100. Accordingly, the predetermined pushing force exerted on the ear when the base 152 of the device 150 is disposed in the operative position of either FIG. 18 or 19 is capable of a predetermined decibel increase in the sound pressure level (SPL) of the ear. This increase in decibels of the SPL allows an enhanced hearing of the user's ear associated with the appropriately positioned hearing assistance device 150.

As should be apparent the cooperative structuring of different ones of the hearing assistance device 150 and there corresponding bases 152 may result in the development of different pushing or positioning forces being exerted on the ear. By way of example only, an adult male may have a larger ear structure than that of a small child. Accordingly, a greater pushing force may be required in order to position the adult's ear into an appropriate hearing enhanced orientation in order to sufficiently increase decibels of the SPL of the adult's ear.

In contrast, a smaller, possibly more flexible, ear of a child may require significantly less pushing or positioning force being exerted on the ear in order to accomplish an appropriate hearing enhanced orientation of the ear and an adequate increase in the decibels of the SPL. Therefore, biasing capabilities as well as other cooperative structural features of the base 152, specifically including the head segment 154 and the ear segment 156, may differ between devices 150 when used for a child or when used for an adult. Based on the recognized proposition that an increase of the pushing force is determinative of an increase of the hearing enhanced orientation and further that the specific hearing enhanced orientation will be determinative of an increase in decibels of the sound pressure level of the affected ear, the structuring of the biasing capabilities or reinforcement rib 158 may vary.

By way of example and with specific reference to FIG. 17, various dimensions of the various parts of the base 152 of the hearing assistance device 150 are structured to accomplish the preferred range of decibel increase in the sound pressure level of the affected ear. More specifically, head segment 154 includes a larger transverse dimension along a majority of its length than that of the ear segment 156. As such, the transverse dimension of the head segment 154 is generally about three quarters of an inch (0.787 in.). In addition, the length of the head segment 154 is generally about three quarters of an inch (0.743 in.) as it extends between the junction 160 with the ear segment and the free end or extremity 162 of the head segment 154.

As also represented in FIG. 17, the ear segment 156 comprises an elongated, at least partially linear configuration, wherein the transverse dimension thereof is substantially continuous along its length from the junction or connection 160 with the head segment 154 to an outer free end or extremity 164. As such, the transverse dimension of the ear segment is generally about one quarter of an inch (0.250 in.). In cooperation therewith, one practical example of the base 152 includes the length of the ear segment 156 being generally about three quarters of an inch (0.741 in.). Cooperative structuring and configuring of the reinforcement of the rib 158 in accord with the preferred embodiment of FIG. 17 comprises the length of the reinforcement rib 158 being generally about 1½ inches (1.484 in.), wherein the transverse dimension is generally about one quarter of an inch along at least a portion of its length.

As practically used and applied, different ones of the hearing assistance devices 150, including the bases 152, may have different biasing capabilities resulting in different "Spring Rates" or "pushing or positioning" forces being exerted on the ear 100, as explained in greater detail hereinafter with regard to the accompanying Table of testing results. Accordingly, the hearing assistance device is structured to develop a pushing or positioning force or "Spring Rate" sufficient to create a hearing enhanced orientation of the ear 100 capable of an increase in the decibels of the sound pressure level (SPL) of the ear of generally between five decibels and twenty decibels.

In addition to the above, relevant testing was conducted on at least one structural embodiment of a hearing assistance device 150, as represented in FIG. 17, having substantially the same dimensions as set forth above. The data obtained from such testing, as provided in the following TABLE, indicates that the exertion of different and increasing amounts of weight or "Load", results in correspondingly increasing amounts of "deflection". However, the rigidity and/or biasing capabilities of the device 150 produces a substantially constant pushing or positioning force represented as Spring Rate.

For purposes of clarity, the following Table represents the amount of weight or "Load" applied to the hearing assistance device 150, being represented in both total ounces (ttl oz) and pounds (Lbs). It is noted that the designation of the "Load" in lbs is rounded-off, i.e. 0.24 ttl-oz and 0.36 ttl-oz are both approximately 0.02 lbs.

The results indicate that a substantially consistent average of 0.60 pounds/per inch (lb/in) of "Spring Rate" was developed in the hearing assistance device 150. As such, the "Spring Rate" developed by the deflection of the device 150, such as when disposed in the operative position behind the user's ear is substantially equivalent to the amount of "pushing or positioning" force exerted on the ear, which serves to position it in an appropriate of predetermined "hearing enhanced orientation" to assist the user in hearing.

TABLE

| Weight | Load | | Deflection | Spring Rate |
|---|---|---|---|---|
| No. | ttl oz | Lbs | in | Lbs/in |
| 1 | 0.12 | 0.01 | 0.02 | 0.38 |
| 2 | 0.24 | 0.02 | 0.03 | 0.60 |
| 3 | 0.36 | 0.02 | 0.04 | 0.56 |
| 4 | 0.46 | 0.03 | 0.05 | 0.58 |
| 5 | 0.58 | 0.04 | 0.06 | 0.60 |
| 6 | 0.70 | 0.04 | 0.08 | 0.55 |
| 7 | 0.80 | 0.05 | 0.09 | 0.56 |
| 8 | 0.92 | 0.06 | 0.10 | 0.58 |
| 9 | 1.02 | 0.06 | 0.11 | 0.58 |
| 10 | 1.14 | 0.07 | 0.12 | 0.59 |
| 11 | 1.26 | 0.08 | 0.13 | 0.61 |
| 12 | 1.36 | 0.09 | 0.14 | 0.61 |
| 13 | 1.48 | 0.09 | 0.15 | 0.62 |
| 14 | 1.60 | 0.10 | 0.16 | 0.63 |
| 15 | 1.70 | 0.11 | 0.17 | 0.63 |
| 16 | 1.82 | 0.11 | 0.18 | 0.63 |
| 17 | 1.94 | 0.12 | 0.19 | 0.64 |
| 18 | 2.04 | 0.13 | 0.20 | 0.64 |
| Average Spring Rate Lb/in → | | | | 0.60 |

Accordingly, the hearing assistance device 150 is structured to include sufficient rigidity and/or biasing capabilities to exert an adequate pushing or positioning force on the ear. More specifically, when bent or curved into the appropriate configuration substantially corresponding to the operative position and placed in the operative position behind the user's ear, the rigidity and/or biasing capabilities of the device 150, will be such as to exert a sufficient positioning or pushing force on the ear to dispose it in the appropriate "hearing enhanced orientation" to accomplish a predetermined or desired increase in decibels of the sound pressure level (SPL).

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A device structured to facilitate hearing in a user's ear, said device comprising:
 a base having an elongated configuration of sufficient length to assume an operative position relative to the ear, said base including an head segment and a ear segment each including an adhering structure disposed thereon, said operative position comprising said head segment and said ear segment respectively and concurrently disposed in confronting engagement with a rear surface of the ear and an adjacent portion of the head,
 said base including biasing capabilities structured to produce a predetermined positioning force on the ear by said ear segment when said base is in said operative position, and
 said predetermined positioning force sufficient to dispose the ear into a hearing enhanced orientation capable of a predetermined decibel increase in a sound pressure level (SPL) of the ear.

2. A device as recited in claim 1 wherein said base and said biasing capabilities are cooperatively structured to define said hearing enhanced orientation as an outwardly and forwardly positioning of the ear relative to the adjacent portion of the head.

3. A device as recited in claim 2 wherein said base and said biasing capabilities are cooperatively structured to define said hearing enhanced orientation as being dependent on the strength of said positioning force.

4. A device as recited in claim 2 wherein said head segment, said ear segment and said biasing capabilities are cooperatively structured to establish a decibel increase in the sound pressure level as being dependent on an increase in said hearing enhanced orientation.

5. A device as recited in claim 4 wherein an increase in said positioning force is determinative of an increase in said hearing enhanced orientation.

6. A device as recited in claim 1 wherein a strength of said positioning force is determinative of said hearing enhanced orientation; said hearing enhanced orientation relative to the user's head being determinative of an increase or a decrease of the decibels of the sound pressure level.

7. A device as recited in claim 6 wherein said positioning force is sufficient to establish an increase of at least 5 decibels in the sound pressure level.

8. A device as recited in claim 6 wherein said positioning force is sufficient to establish an increase of at least 10 decibels in the sound pressure level.

9. A device as recited in claim 6 wherein said positioning force is sufficient to establish an increase of about 20 decibels in the sound pressure level.

10. A device as recited in claim 6 wherein said positioning force is sufficient to establish an increase of generally between 5 decibels and 20 decibels of the sound pressure level.

11. A device as recited in claim 10 wherein said base and said biasing capabilities are cooperatively structured to define a positioning force of generally about 0.60 pounds per inch and greater than generally about 0.40 pounds per inch.

12. A device as recited in claim 1 wherein said head segment comprises a larger transverse dimension along a majority of its length than that of said ear segment.

13. A device as recited in claim 12 wherein said transverse dimension of said head segment is generally about ¾ of an inch.

14. A device as recited in claim 13 wherein a length of said head segment is generally about ¾ of an inch between said ear segment and an outer extremity of said head segment.

15. A device as recited in claim 12 wherein said ear segment comprises an elongated configuration of substantially continuous transverse dimension along its length substantially from said head segment to a free, outer extremity of said ear segment.

16. A device as recited in claim 15 wherein said transverse dimension of said head segment is at least generally about ¼ inch.

17. A device as recited in claim 16 wherein said transverse dimension of said head segment is at least general about ¾ inch.

18. A device as recited in claim 12 wherein said biasing capabilities comprise a biasing rib having an elongated configuration and structured to include an inherent bias.

19. A device as recited in claim 18 wherein said biasing rib extends along substantially the entire length of said base including that of said ear and head segments.

20. A device as recited in claim 19 wherein the length of said biasing rib is generally about 1½ inches.

21. A device as recited in claim 1 wherein said base comprises an indicator disposed thereon and indicative of a configuring of said base to substantially conform to said operative position.

* * * * *